United States Patent [19]

Gusakov

[11] Patent Number: 4,969,459
[45] Date of Patent: Nov. 13, 1990

[54] INFRARED HEATING SYSTEM FOR SURGICAL PATIENTS

[75] Inventor: Ignaty Gusakov, East Aurora, N.Y.

[73] Assignee: Gaymar Industries, Inc., Orchard Park, N.Y.

[21] Appl. No.: 503,101

[22] Filed: Mar. 30, 1990

Related U.S. Application Data

[63] Continuation of Ser. No. 237,164, Aug. 29, 1988, abandoned.

[51] Int. Cl.$^5$ .............................................. A61F 7/00
[52] U.S. Cl. .................................... 128/399; 128/736; 128/905; 128/419 N; 600/22
[58] Field of Search ............... 128/736, 395, 399, 905, 128/419 N; 600/22

[56] References Cited

U.S. PATENT DOCUMENTS

| | | | |
|---|---|---|---|
| 3,667,476 | 6/1972 | Muller | 128/399 |
| 3,789,853 | 2/1974 | Reinhard | 128/399 |
| 4,034,740 | 7/1977 | Atherton et al. | 600/22 |
| 4,397,314 | 8/1983 | Vaguine | 128/399 |
| 4,750,474 | 6/1988 | Dukhan et al. | 128/205.26 |

FOREIGN PATENT DOCUMENTS 2045978  7/1980  United Kingdom ................. 600/22

*Primary Examiner*—Edward M. Coven
*Assistant Examiner*—Valerie Szczepanik
*Attorney, Agent, or Firm*—Witherspoon & Hargest

[57] ABSTRACT

An apparatus for the infrared heating and warming of post-anesthetic surgical patients is disclosed. The system includes a plurality of infrared heat lamps controlled by plural patient temperature sensors in a closed-loop control system for providing safe, controlled warming of a patient following anesthesia and surgery. Signals from the temperature sensors are averaged and compared against an average temperature setpoint to provide control signals for the heat lamp control network. Low and high temperature alarms are provided for patient safety.

10 Claims, 1 Drawing Sheet

INFRARED HEATING SYSTEM FOR SURGICAL PATIENTS

This application is a continuation of application Ser. No. 237,164, filed Aug. 29, 1988, now abandoned.

BACKGROUND OF THE INVENTION

1. Field of the Invention

The present invention relates to devices for the warming of post-anesthetic surgery patients to reduce or stop their shivering during initial post-operative recovery when the patients are still under the influence of the anesthesia administered prior to and during the operation.

It has been noted by hospital personnel that one frequent side effect of anesthesia in surgical patients is an uncontrollable shivering by these patients as the effects of the anesthesia are wearing off, and the patient's body attempts to warm itself back to a normal temperature to counteract the reduction of body temperature which was caused by the anesthesia during the operation. 2. Description of the Prior Art Early attempts to warm such patients to reduce or stop their shivering included wrapping them in blankets, but this method did more harm than good for patients with sore and tender surgical sites.

What was needed was a warming method which did not involve direct contact with the patient, one which could provide the patient with warmth without causing discomfort at the same time.

U.S. Pat. Nos. 3,089,033 to Fujisawa and 3,789,853 to Reinhard disclose prior art systems for the use of infrared heat energy for the warming and treating of living tissue. Both of these patents express concern for the control of their heating systems to prevent injury to the patient, and offer rather primitive solutions to the problem.

It is an object of this invention to provide an infrared heating system for post-anesthetic patients with a fail-safe control system to preclude possible patient injury.

It is another object of this invention to provide a closed-loop temperature control system to maintain patient temperature within a preselected temperature range.

It is yet another object of this invention to include a plurality of temperature sensors to measure patient temperature, such that the failure of one sensor will not cause failure of the entire heating system.

These and other objects of this invention will be better understood by reference to the detailed description of the preferred embodiment as set forth below.

SUMMARY OF THE INVENTION

The present invention is a warming system for post-anesthetic patients coming out of surgery. The system includes a plurality of infrared lamps and a plurality of patient temperature sensor including a closed-loop control system for monitoring and controlling patient temperature within a predetermined temperature range. To ensure patient safety, the system is designed to be fail-safe. The signals generated by the multiple temperature sensors are averaged, such that failure of a single sensor will not change the average signal significantly. In case of over-heating of a patient beyond a predetermined maximum threshold temperature, the entire system will be turned off. Constant hot-cold cycling of the patient's temperature is avoided by providing a minimum lamp output level which coincides with normal patient heat loss rather than cycling the lamps completely off during the heating cycle.

DETAILED DESCRIPTION OF THE PREFERRED EMBODIMENT

Figure 1:
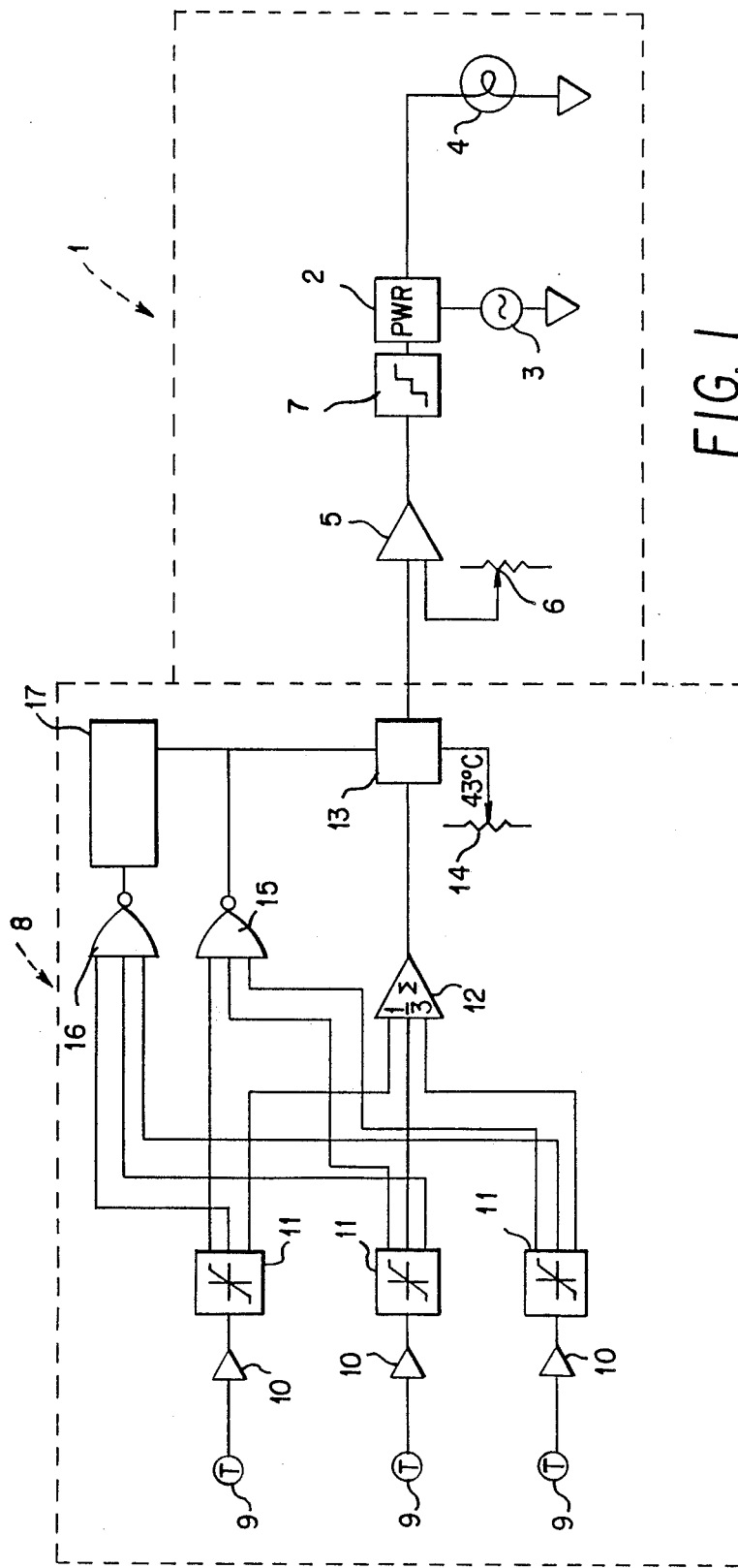
FIG. 1 is a block diagram of the basic circuitry of the invention.

Referring to FIG. 1, the preferred embodiment of the infrared heating system of the instant invention is shown as a block circuit diagram to illustrate the major components thereof, and to show their associated electrical interconnections. The output control network 1 includes a power supply 2 connected to a standard source of alternating current 3 for powering a plurality of infrared heat lamps 4 arranged to irradiate the patient under treatment (not shown). Also included in the output control network is control amplifier 5 provided with a normal bias adjustment 6, which control amplifier generates a control signal to acutate the three-level power control means 7 associated with lamp power supply 2.

The input signal for control amplifier 5 is derived from the control logic section 8 of the system circuitry which, in combination with the output control network, creates a closed-loop control system for the infrared heat lamps 4. The control logic begins with a plurality of temperature measuring transducers 9, which may be thermistors, resistance thermometers or the like. These transducers are attached to the patient being treated, and generate signals corresponding to the patient's skin temperature. The signals from transducers 9 are fed through a plurality of individual signal conditioning amplifiers 10 to a like plurality of individual limiter circuits 11. The signal conditioning amplifiers allow proper scaling of the temperature signals, and the limiters allow the adjustment of high and low temperature threshold levels for patient protection. For example, detection of a high temperature likely to cause patient injury can be used to sound an alarm and turn off the power supplied to lamps 4; and detection of a low temperature may be indicative of system or temperature sensor malfunction, dislodgment or the like can be used to sound an alarm so that the malfunction can be corrected.

If the signals sensed by the limiter circuits 11 are within the bounds set therein, the plural signals, three in this preferred case, are sent to the averaging amplifier 12. This system is designed with a certain redundancy which enhances overall reliability. If one sensor fails, the limiter will saturate at its limit value and its voltage will be added to the two functioning sensor signals. Averaging of the three signals from the transducers or sensors 9, coupled with the high and low threshold limits placed on the signals, allows one probe to fail or malfunction without seriously affecting control of the entire system. Failure of a sensor will still produce a usable average with only a slight offset error.

Assuming that the signal from averaging amplifier 12 is within the bounds of the upper and lower threshold of the limiter circuits 11, the signal is applied to the control circuit 13, in which it is compared with the adjustable average temperature setpoint from variable resistor 14, and an appropriate signal is sent to control amplifier 5 of the output control network 1.

High threshold alarm signals from limiters 11 are applied to logic gate 15, which, upon sensing an over temperature condition, will cause control circuit 13 to send a full off signal to control amplifier 5 to turn the heat lamps 4 completely off. Low threshold alarm signals from limiters 11 are applied to logic gate 16, which upon sensing a low threshold signal will signal an alarm 17.

The closed-loop feedback control system of this invention includes not only the electrical energy circuitry described above, but also the radiant energy connection between the heat lamps 4 and the temperature sensors 9. It is the heat produced by the lamps 4 which changes the skin temperature of the patient, which temperature is measured by sensors 9 which generate signals corresponding to that temperature which are used to control the lamps in a closed-loop fashion.

Figure 2:
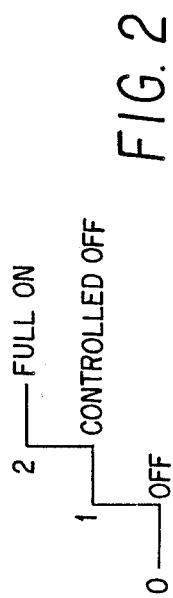
FIG. 2 is a schematic diagram of the three operating points of the closed-loop control system of the invention.

Referring to FIG. 2, there are three control levels for power supply 2. The first control level is labelled O, or FULL OFF. This position supplies no current to the heating system whatsoever. This is the control level in effect when the heating system is not in use, and the level to which the system is controlled to if an over temperature condition is sensed. A second control level is labelled 2, or FULL ON. This control level is activated when the system is first turned on, and whenever an increase in temperature is required as sensed by the control logic circuitry. This FULL ON position provides the most rapid response time for the heat lamps, since the main objective of the overall heating system is to warm the patient in a safe and expeditious manner. The third control level, 1 or CONTROLLED OFF, is a standby position for the heat lamps during the ON-OFF cycling caused by the control logic. If, upon sensing of the maximum skin temperature being reached under the lamps the are turned to FULL OFF, an immediate cooling of the patient will commence. To help avoid this, and to aid in stabilizing the patient's temperature, the CONTROLLED OFF level allows the lamps to generate just enough heat to compensate for the normal heat loss of a human body. This will prevent the skin surface from cooling excessively, and prevent the patient from sensing a pronounced cooling effect as the heat lamps are modulated by the control logic from ON to OFF. The lamps 4 will go from CONTROLLED OFF to FULL ON to quickly begin the warming process.

The proper utilization of the invention will be described with regard to FIG. 1. The patient to be warmed is placed under the heat lamps 4. Temperature sensors 9 are attached to the patient te sense skin temperature. Several methods of attachment are contemplated. First, the three sensors may be encapsulated and packaged as a smalll, compact button, thus facilitating attachment to a single location, such as the sternum. Second, the sensors may be attached to the ends of short pigtail wires two to four inches in length wich come together in a cable bundle. This method requires three attachment locations on the patient, but may provide a more accurate average temperature signal. A third possibility is the use of an infrared detector as a temperature sensor. This device can sense skin temperature remotely without contacting the patient. The signal generated by such a device may be integrated into the control system logic eithers as one of the three feedback signals or as an additional override safety signal.

Once the sensors 9 are attached, and the average temperature setpoint resistor is adjusted, the system is turned on. When the temperature signals from transducers 9 reach the upper limits set in limiters 11, a signal is sent by control circuit 13 to control amplifier 5, and the power supply control level goes to CONTROLLED OFF while the patient cools and temperature stabilizes. This cycle is repeated until the patient's temperature stabilizes near normal body temperature.

If a low limit temperature is sensed by any of the limiters 11, indicating a probe malfunction, dislodgment or the like, an alarm 17 will sound to allow attending personal to correct the problem, but the heating system will continue to function. If, on the other hand, a high limit temperature is sensed, an alarm 17 will sound and the heating system will be set to FULL OFF for patient protection until the problem can be rectified.

While the foregoing description places particular emphasis on the preferred embodiment of the invention, it will be readily recognized by those skilled in the art that modifications may be made without departing from the spirit and scope of the invention as it is defined by the appended claims.

We claim:

1. An infrared heating system to stop shivering in a post-anesthetic patient following surgery, comprising:

a plurality of infrared heat lamps and an associated power source for operating said lamps;

a control system for controlling the duration and intensity of the operation of said lamps, said control system comprising means including a plurality of temperature sensors for sensing the temperature of said skin and generating respective temperature signals corresponding to the temperature sensed by each temperature sensor;

means including a plurality of individual signal conditioning amplifiers each coupled to a respective temperature sensor of said plurality of temperature sensors for receiving and scaling a respective temperature signal and for producing a respective first output signal;

means including a plurality of individual limiter circuits each coupled to a respective signal conditioning amplifier for receiving a respective first output signal and limiting said respective first output signal such that if said respective first output signal is within high threshold and low threshold bounds set by the respective individual limiter circuit said respective first output signal will be sent unchanged to an averaging amplifier, and if said respective first output signal is not within said bounds set by the respective individual limiter circuit said respective individual limiter circuit will saturate at a preset limit value, which will be sent to said average amplifier;

said averaging amplifier is coupled to each of said limiter circuits for so receiving therefrom unchanged first output signals, and any saturation voltage, for producing an averaged output signal; and means including a control circuit which is coupled to said averaging amplifier for receiving said averaged output signal for comparison with an average temperature setpoint and producing a corresponding second output signal which is applied to said control system to provide closed-loop temperature control of said patient by controlling the operation of said lamps.

2. The infrared heating system of claim 1 further including a first logic gate coupled to each limiter circuit and to said control circuit, and further, wherein if any of said first output signals are not within said bounds set by its respective limiter circuit then any signal amplitude beyond said high threshold of said preset limit value will be applied to said first logic gate for causing said control circuit to send a full off signal to said control system to turn said heat lamps completely off.

3. The infrared heating system of claim 2 wherein said first logic gate is coupled to an alarm.

4. The infrared heating system of claim further including a second logic gate coupled to each limiter circuit and an alarm, and further wherein if any of said first output signals are not within said bounds set by it respective limiter circuit then any signal amplitude beyond said low threshold of said preset limit value will be applied to said alarm for signaling said alarm.

5. The infrared heating system of claim 1 further including a variable resistor coupled to said control circuit and wherein said average temperature setpoint is adjustable by said variable resistor.

6. The infrared heating system of claim 1 wherein each temperatue sensor of said plurality of temperature sensors provides feedback to produce a signal for the control system and wherein the feedback of less than all of said temperature sensors will produce signals to maintain said control system.

7. An infrared heating system as described in claim 1, in which said control system for controlling the duration and intensity of the operation of said lamps includes a full on operating level for maximum heating and minimum response time, and a controlled off operating level which allows said lamps to generate just enough heat to compensate for the normal heat loss experienced by a human body at rest.

8. An infrared heating system as described in claim 1, in which said temperature sensors are resistance thermometers.

9. An infrared heating system as described in claim 1, in which said temperature sensors are thermistors.

10. An infrared heating system as described in claim 1, in which said plurality of temperature sensors are contained in a single housing to facilitate attachment to a patient.

* * * * *